United States Patent [19]

Ellory et al.

[11] Patent Number: 5,145,867
[45] Date of Patent: Sep. 8, 1992

[54] NAPHTHYLALKYLAMINO-SUBSTITUTED SULFAMOYLBENZOIC ACID DERIVATIVES, AND THE USE THEREOF AS MEDICINES

[75] Inventors: John C. Ellory, Oxford, United Kingdom; Heinrich C. Englert; Hans-Jochen Lang, both of Hofheim am Taunus, Fed. Rep. of Germany; Dieter Mania, Königstein; Wulf Merkel, Kelkheim, both of Fed. Rep. of Germany

[73] Assignee: Hoechst Aktiengesellschaft, Frankfurt am Main, Fed. Rep. of Germany

[21] Appl. No.: 505,466

[22] Filed: Apr. 6, 1990

[30] Foreign Application Priority Data

Apr. 8, 1989 [DE] Fed. Rep. of Germany ....... 3911549

[51] Int. Cl.$^5$ ............... A61K 31/38; A61K 31/235; C07D 333/34; C07C 323/22
[52] U.S. Cl. .................... 514/445; 514/447; 514/510; 514/534; 514/535; 514/562; 549/65; 549/68; 560/10; 562/427
[58] Field of Search ............ 560/10; 562/427; 514/510, 562, 445, 447, 448, 464, 534, 535; 549/65, 68

[56] References Cited

U.S. PATENT DOCUMENTS 4,266,077  5/1981  Conrow et al. .............. 562/427

FOREIGN PATENT DOCUMENTS 2654795  6/1978  Fed. Rep. of Germany .
1434405  5/1976  United Kingdom .

OTHER PUBLICATIONS

John Wiley, Diuretics, Chemistry, Pharmacology and Medicine, (1983), p. 162.

*Primary Examiner*—Jose G. Dees
*Assistant Examiner*—Vera C. Clarke
*Attorney, Agent, or Firm*—Finnegan, Henderson, Farabow, Garrett and Dunner

[57] ABSTRACT

Naphthylalkylamino-substituted sulfamoylbenzoic acid derivatives, processes for the preparation thereof and the use thereof as medicines.

Compounds I

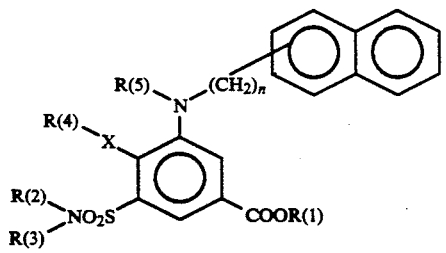

R(1) hydrogen, $(C_1-C_4)$-alkyl and Na, K, $NH_4$, Ca, Mg,
R(2) and R(3) hydrogen, alkyl groups which can also be linked together in a ring,
X oxygen, sulfur, SO, $SO_2$, NR(6) [with R(6)=hydrogen-alkyl], $CH_2$, CO, or a bond,
R(4) phenyl, thienyl, which are unsubstituted or substituted
R(5) hydrogen, $(C_1-C_4)$-alkyl,
n 1, 2, 3 or 4, where the naphthyl system is unsubstituted or substituted like the phenyl radical of R(4), and where X and R(4) together can also be Cl are medicaments for treating sickle-cell anemia.

4 Claims, No Drawings

NAPHTHYLALKYLAMINO-SUBSTITUTED SULFAMOYLBENZOIC ACID DERIVATIVES, AND THE USE THEREOF AS MEDICINES

The invention relates to naphthylalkylamino-substituted sulfamoylbenzoic acid derivatives and processes for the preparation thereof and the use thereof as medicines for sickle-cell anemia. In the compounds I according to the invention

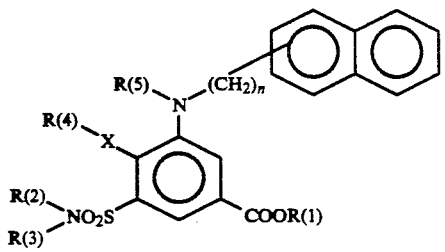

the following substituents have the following meanings:

R(1) hydrogen, ($C_1$–$C_4$)-alkyl and Na, K, $NH_4$, Ca, Mg,

R(2) and R(3) hydrogen, identical or different ($C_1$–$C_4$)-alkyl groups which can also be linked together in a ring, X oxygen, sulfur, SO, $SO_2$, NR(6) [with R(6)=hydrogen or ($C_1$–$C_2$)-alkyl], $CH_2$, CO, or a bond, R(4) phenyl, thienyl, which are unsubstituted or substituted by 1 to 2 substituents which are selected from the group comprising F, Cl, Br, ($C_1$–$C_2$)-alkyl, ($C_1$–$C_2$)-alkoxy, methylenedioxy, S-($C_1$–$C_2$)-alkyl, R(5) hydrogen, ($C_1$–$C_4$)-alkyl, n 1, 2, 3 or 4, where the naphthyl system is unsubstituted or substituted like the phenyl radical of R(4), and where X and R(4) together can also be Cl.

Preferred compounds I are those in which

R(1) is hydrogen, Na, K, Ca, Mg,

R(2), R(3), R(5) are hydrogen,

X is oxygen or a bond,

R(4) is phenyl, thienyl n is 2.

If R(1) is Na, K, Ca, Mg, the compounds I are in the form of salts.

The invention additionally relates to processes for the preparation of compounds I. These entail a) reacting compounds II

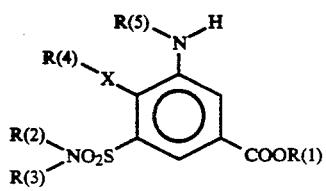

in which R(1) to R(5) and X have the stated meanings, in a manner known per se, with compounds III

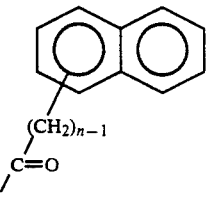

and reducing the resulting compounds V

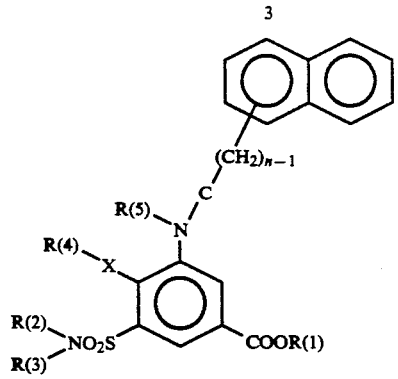

in a manner known per se, to compounds I, or b) reacting compounds II

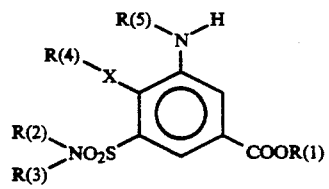

in a manner known per se, with compounds IV

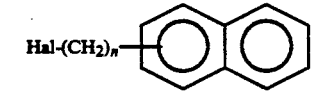

It is also possible during these preparation processes for the two groups R(2) and R(3) together to be the protective groups which are customary in such reactions and whose use and subsequent elimination is described, for example, in German Patent 24 61 601.

The compounds I according to the invention are suitable as medicines for sickle-cell anemia, in that they slow down the shrinkage of erythrocytes and thus counteract a sickle-like deformation of the erythrocytes, which often takes place in the deoxygenated state and, as is known, impedes blood flow through the capillaries. The medicine comprises an effective amount of the compound I and a pharmaceutically acceptable carrier. The compounds I inhibit the KCl symport system on erythrocytes, which—as is known—is activated when there is a reduction in volume of the erythrocytes.

The compounds I according to the invention are suitable for the treatment of acute sickle-cell anemia or else for preventive therapy.

This entails use of at least 0.1 mg/kg of body weight, preferably 0.5 mg, in particular 1 mg/kg of body weight as total daily dose for a person weighing 75 kg, and the maximum daily dose is 10 mg, preferably 5 mg, in particular 1 mg/kg of body weight.

These daily doses can be administered orally, intravenously or rectally, in particular in one or in several doses.

Compounds similar to the compounds I according to the invention, but with phenyl in place of the naphthyl group, are disclosed in DIURETICS, Chemistry, Pharmacology, and Medicine, JOHN WILEY & SONS, New York, Chichester, Brisbane, Toronto, Singapore, 1983, page 162, table 3.46. However, they are described only as diuretics, no mention being made of any other activity.

The compounds I according to the invention have negligible diuretic activity.

The starting compounds II are prepared by the process as is described in German Patent 26 54 795 or else by the process of German Patent 24 61 601.

EXAMPLE 1

3-(2-Naphthylethylamino)-4-phenoxy-5-sulfamoylbenzoic acid

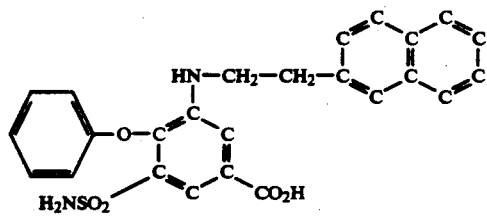

3 g of NaOH pellets are introduced into a suspension of 3 g of methyl 3-(2-naphthylethylamino)-4-phenoxy-5-N,N -dimethylaminomethyleneaminosulfonylbenzoate in 40 ml of ethanol, and the mixture is then stirred at 60° to 70° C. to produce a clear solution. After dilution with 40 ml of water, stirring is continued at 70° C. for half an hour. After the solution has been cooled to about 0° C. it is acidified with excess conc. HCl. The precipitate is filtered off, washed several times with cold water and dried.

Crystals of melting point 270° C.

PREPARATION OF THE STARTING COMPOUNDS a) Methyl 3-(2-naphthylacetamide)-4-phenoxy-5-N,N -dimethylaminomethyleneaminosulfonylbenzoate

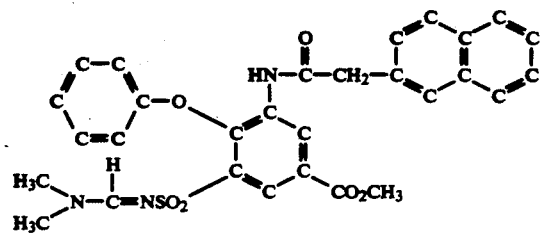

A solution of 18.5 g (0.09 mole) of 2-naphthylacetyl chloride in 65 ml of acetone is added dropwise to a solution of 20 g (0.053 mol) of methyl 3-amino-4-phenoxy -5-N,N-dimethylaminomethyleneaminosulfonylbenzoate in 200 ml of dioxane and 7.3 ml (0.09 mole) of pyridine at 80° C. After stirring at 80° C. for two hours, the solution is cooled, introduced into ice-water and extracted with methylene chloride. The methylene chloride solution is dried over Na$_2$SO$_4$. and then evaporated in vacuo, and the residue is recrystalized from methanol.

Crystals of melting point 127°-128° C.

b) Methyl 3-(2-naphthylethylamino)-4-phenoxy-5-N,N-dimethylaminomethyleneaminosulfonylbenzoate

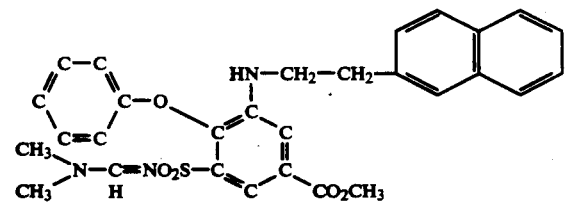

A solution of 1 g (0.026 mole) of NaBH$_4$ in 52 ml of diglyme is added dropwise to a solution of 11.5 g (0.021 mole) of methyl 3-(2-naphthylacetamido)-4-phenoxy -5-N,N-dimethylaminomethyleneaminosulfonylbenzoate in a mixture of 80 ml of diglyme and 4.5 ml (0.035 mole) of BF$_3$ etherate. After stirring at 20° C. for several hours—the progress of the reaction is followed by thin-layer chromatography (silica gel, ethyl acetate/petroleum ether 4:1)—the reaction solution is introduced into ice-water. The precipitate is filtered off with suction, dried and recrystallized several times from ethanol/DMF. Crystals of melting point 159° C.

EXAMPLE 2

3-(1-Naphthylethylamino)-4-phenoxy-5-sulfamoylbenzoic acid

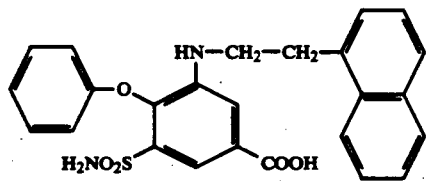

In analogy to Example 1.
White crystals of melting point: 233°-235° C.

EXAMPLE 3

3-(2-Naphthylethylamino)-4-(2-thienyl)-5-sulfamoylbenzoic acid

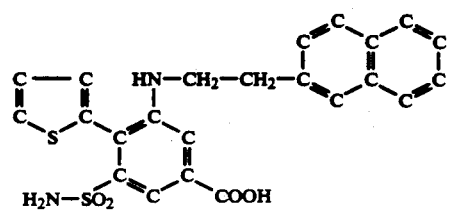

In analogy to Example 1.
Melting point: 208°-209° C.

EXAMPLE 4

4-Chloro-3-(2-naphthylethylamino)-5-sulfamoylbenzoic acid

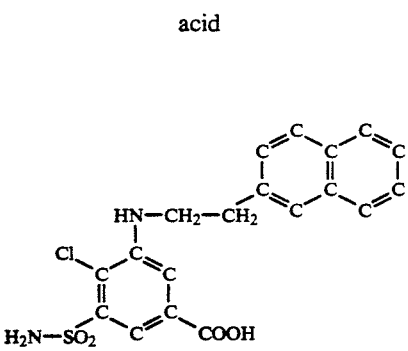

In analogy to Example 1.

Melting point: 230° C.

EXAMPLE 5

3-(2-Naphthylethylamino)-4-phenyl-5-sulfamoylbenzoic acid

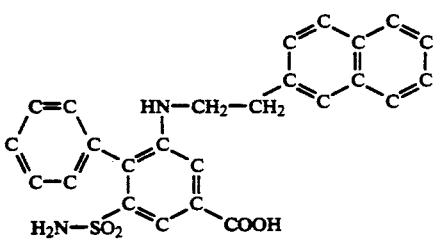

In analogy to Example 1.

Melting point: 223°-224° C.

EXAMPLE 6

3-(1-Naphthylethylamino)-4-phenyl-5-sulfamoylbenzoic acid

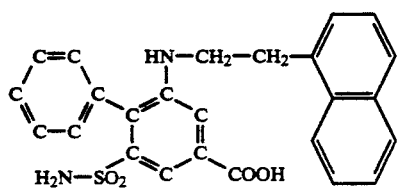

In analogy to Example 1.

Melting point: 217°-218° C.

EXAMPLE 7

3-(1-Naphthylethylamino)-4-(2-thienyl)-5-sulfamoylbenzoic acid

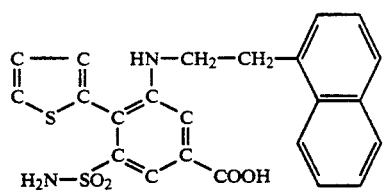

In analogy to Example 1.

Melting point: 192° C.

EXAMPLE 8

4-Chloro-3-(1-naphthylethylamino)-5-sulfamoylbenzoic acid

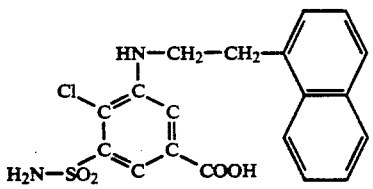

In analogy to Example 1.

Melting point: 151°-152° C.

We claim:

1. A compound I

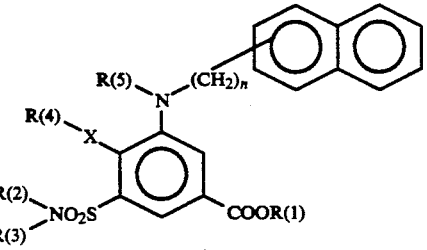

in which the following substituents have the following meaning:

R(1) is hydrogen, $(C_1-C_4)$-alkyl, Na, K, $NH_4$, Ca or Mg,

R(2) and R(3) are hydrogen, or identical or different $(C_1-C_4)$-alkyl groups,

X is oxygen or a bond,

R(4) is phenyl or thienyl

R(5) is hydrogen or $(C_1-C_4)$-alkyl, and n is 1, 2, 3 or 4, where X and R(4) together can also be Cl.

2. A compound as claimed in claim 1, wherein the following substituents have the following meaning:

R(1) is hydrogen, Na, K, Ca or Mg

R(2), R(3) and R(5) are hydrogen,

X is oxygen or a bond,

R(4) is phenyl or thienyl, and n is 2.

3. A pharmaceutical composition for the treatment of sickle-cell anemia comprising an effective amount of the compound I as claimed in claim 1 and a pharmaceutically acceptable carrier.

4. A method for the treatment of sickle-cell anemia, which comprises administration of an effective amount of a compound I as claimed in claim 1 to a person in need of said treatment.

* * * * *